US00PP12453P2

(12) United States Plant Patent
Utecht

(10) Patent No.: US PP12,453 P2
(45) Date of Patent: Mar. 12, 2002

(54) GERANIUM PLANT NAMED 'FISLET'

(75) Inventor: Angelika Utecht, Montabaur (DE)

(73) Assignee: Floris AG, Binningen (CH)

( * ) Notice: Subject to any disclaimer, the term of this patent is extended or adjusted under 35 U.S.C. 154(b) by 0 days.

(21) Appl. No.: 09/772,843

(22) Filed: Jan. 31, 2001

(51) Int. Cl.[7] ..... A01H 5/00
(52) U.S. Cl. ..... Plt./330
(58) Field of Search ..... Plt./330, 328

(56) References Cited

PUBLICATIONS

GTITM UPOVROM Citation for 'Fislet' as per QZ PBR 991263; Sep. 13, 1999.*
Fischer–Schmülling Plant Alliance Catalog featuring 'FISLET' on p. 6 (2001).
Official Gazette of the Community Plant Variety Office Dec. 15, 1999; European Union Application, denomination, decision for 'FISLET'.
German Application for 'FISLET' Nov. 15, 1998.
German Proposed Denomination for 'FISLET' Aug. 15, 1999.
Plant Varieties Journal, Jan. 2001, No. 38, pp. 52–53(Canada).

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fislet', as described and illustrated, and particularly characterized by the combined features of bright orange-red, semi-double flowers, large umbels and strong peduncles, medium green foliage with strong zonation, vigorous growth, and relatively tall, uniform plant habit.

1 Drawing Sheet

BACKGROUND OF THE INVENTION

The present invention comprises a new and distinct cultivar of geranium, botanically known as *Pelargonium zonale,* and hereinafer referred to by the cultivar name 'Fislet'.

'Fislet' is a product of a planned breeding program which had the objective of creating new geranium varieties with red flower color and vigorous growth for outdoor planting/landscaping. 'Fislet' originated from a hybridization made by the inventor Angelika Utecht in a controlled breeding program in Galdar, Gran Canaria, Spain, in 1994.

The female parent was a hybrid seedling, no. 2061-15 (unpatented), having red, semi-double flowers, medium-green foliage with strong zonation and tall plant habit. The male parent of 'Fislet' was a hybrid seedling, no. 1262-8 (unpatented), which was characterized by red single-type flowers, dark-green foliage, and relatively compact habit.

'Fislet' was selected as one flowering plant within the progeny of the stated cross by Angelika Utecht in 1995 in a controlled environment in Galdar, Gran Canaria, Spain.

The first act of asexual reproduction of 'Fislet' was accomplished when vegetative cuttings were taken from the initial selection in the fall of 1995 in a controlled environment in Galdar, Gran Canaria, Spain, by, or under the supervision of, Angelika Utecht.

Horticultural examination of plants grown from cuttings of the plant initiated in May 1997 in Hillscheid, Federal Republic of Germany, and continuing thereafter, has demonstrated that the combination of characteristics as herein disclosed for 'Fislet' are firmly fixed and are retained through successive generations of asexual reproduction.

'Fislet' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fislet' in combination distinguish this geranium as a new and distinct cultivar:

1. Bright orange-red, semi-double flowers;
2. Large umbels borne high above the foliage;
3. Medium green foliage with strong zonation;
4. Vigorous growth, and relatively tall, but well-branched plant habit;
5. Medium (mid season) spring flowering response; and
6. Relatively rich flowering throughout the summer.

Of the many commercial cultivars known to the present inventor, the most similar in comparison to 'Fislet' is the variety 'Fisgrand', U.S. Plant Pat. No. 8,760. In comparison to 'Fisgrand', 'Fislet' has a slightly more intense flower color, taller plant habit, and higher flower production during the summer.

BRIEF DESCRIPTION OF THE DRAWING

The accompanying photographic drawing shows typical flower and foliage characteristics of 'Fislet' with colors being as true as possible with an illustration of this type. The measurements were taken in Langley, British Columbia, Canada on Jul. 20, 2000, 15 weeks after planting of rooted cuttings into 6 inch pots. The plants had not been pinched.

In the following description color references are made to The Royal Horticultural Society Colour Chart (R.H.S.). The color values were determined indoors from plants developed in a green-house in May 2000 in Hillscheid, Germany.

Classification:

*Botanical.*—A hybrid of the species *Pelargonium zonale* L'Hérit.

*Commercial.*—Zonal geranium, cv. 'FISLET'.

Inflorescence:

*Umbel.*—Shape: Semi-spherical. Average diameter: 128 mm. Average depth: 65–70 mm. Peduncle length: 167 mm. Peduncle color: Light green, from RHS 143 B to RHS 143 C. Pedicel length: 37 mm. Pedicel color: Base is green, RHS 143 B, middle is brownish-red, from RHS 179 B to RHS 179 A, and the upper end is RHS 60 A, with intensity inreasing from the lower to upper end. Number of flowers per umbel: About 30–40. Lastingness of the umbel: Approximately 18–20 days at 18° C.

*Corolla.*—Average diameter: 47 mm. Form: Semi-double. Shape: Round. Number of petals: 8–10. Size of petals: Upper petals are 27–30 mm long, 21–23 mm wide, lower petals are 25–28 mm long, 20–23 mm wide. Shape of petals: Obovate, attenuate base, upper end rounded, margin entire (occasionally divided by a notch). Number of petaloids: 0–1. Color of petaloids: Upper surface RHS 40 A, lower surface RHS 43 C. Color (general tonality from a distance of three meters): Bright orange-red. Color of upper petals: From RHS 40 A to RHS 43 A. Markings of upper peals: No markings or very weak darker red stripes (veins), RHS 46 B. Color of lower petals: From RHS 40 A to RHS 43 A, no markings. Color of lower surface of petal: About RHS 40 B. Color of sepals: Outer surface is green, RHS 137 D, with reddish-brown base, RHS 181 A, inner surface is light green, RHS 143 A, with base RHS 179 A. Number of sepals: 5–6. Size of sepals: 10–12 mm in length, 4–5 in diameter for the largest upper sepal, 2–3 mm in diameter for other sepals. Shape of sepals: Linear to lanceolate, acute tip, base truncate, surface with weak, short pubescence, margin entire.

*Bud:* (*just before petals unfold*).—Shape: Broad elliptical. Color (lower part — sepals): Mainly green, RHS 137 D, weak reddish spot RHS 179 A at the base. Color (upper part — petals): Orange-red, RHS 43 A. Length: 14 mm. Width: 10 mm.

*Reproductive organs.*—Androecium: 5–7 fertile anthers, whitish to light pink filaments, orange pollen, RHS 30 A, plentiful production of pollen. Gynoecium: 5–6-lobed stigma, dark red, from RHS 46 A to RHS 43 B, style and stigma, one pistil per flower. Fertility/seed set: A few seeds are developed, oblong, 4–5 mm long, brown, RHS 177 B.

*Spring flowering response period.*—In Hillscheid, Germany, in 2000 plants had on average 1.0 flowers opened 8 weeks after planting of rooted cuttings.

*Outdoor flower production.*—Relatively rich flowering for a variety that develops huge umbels the flower count in 2000 in Hillscheid, Germany, indicated about 3–4 inflorescences per plant in mid May.

*Durability.*—Good stability of flower color, only moderately susceptible to burning and scorching by the sun for this flower color group, good rain resistance.

*Lastingness of the individual bloom.*—Approximately 8 days at 18° C.

*Fragrance.*—None.

Plant:

*Foliage.*—Form: Kidney-shaped, with weak lobes. Margin: Bicrenated. Base: Cordate with open gap between lower lobes. Texture: Slightly velvety. Size of leaf: 96 mm wide, 55 mm long. Color of upper surface: Medium-green, approximately from RHS 137 B to RHS 137 C. Color of undersuface: RHS 137 D. Color of zonation: Strong, brown, approximately RHS 166 A. Color of petioles: RHS 143 C. Size of petioles: 55–65 mm long, 3 mm wide.

*General appearance and form.*—Stem color: Green, RHS 143 A. Internode length: 20–30 mm. Branching pattern: 6.7 branches. Plant size: 27.7 cm, as measured from the base of the stem to the surface of the foliage canopy, without inflroescences, 41.8 cm wide.

*Disease/pest resistance/susceptibility.*—No observations made to date.

I claim:

1. A new and distinct cultivar of geranium plant named 'Fislet', as described and illustrated.

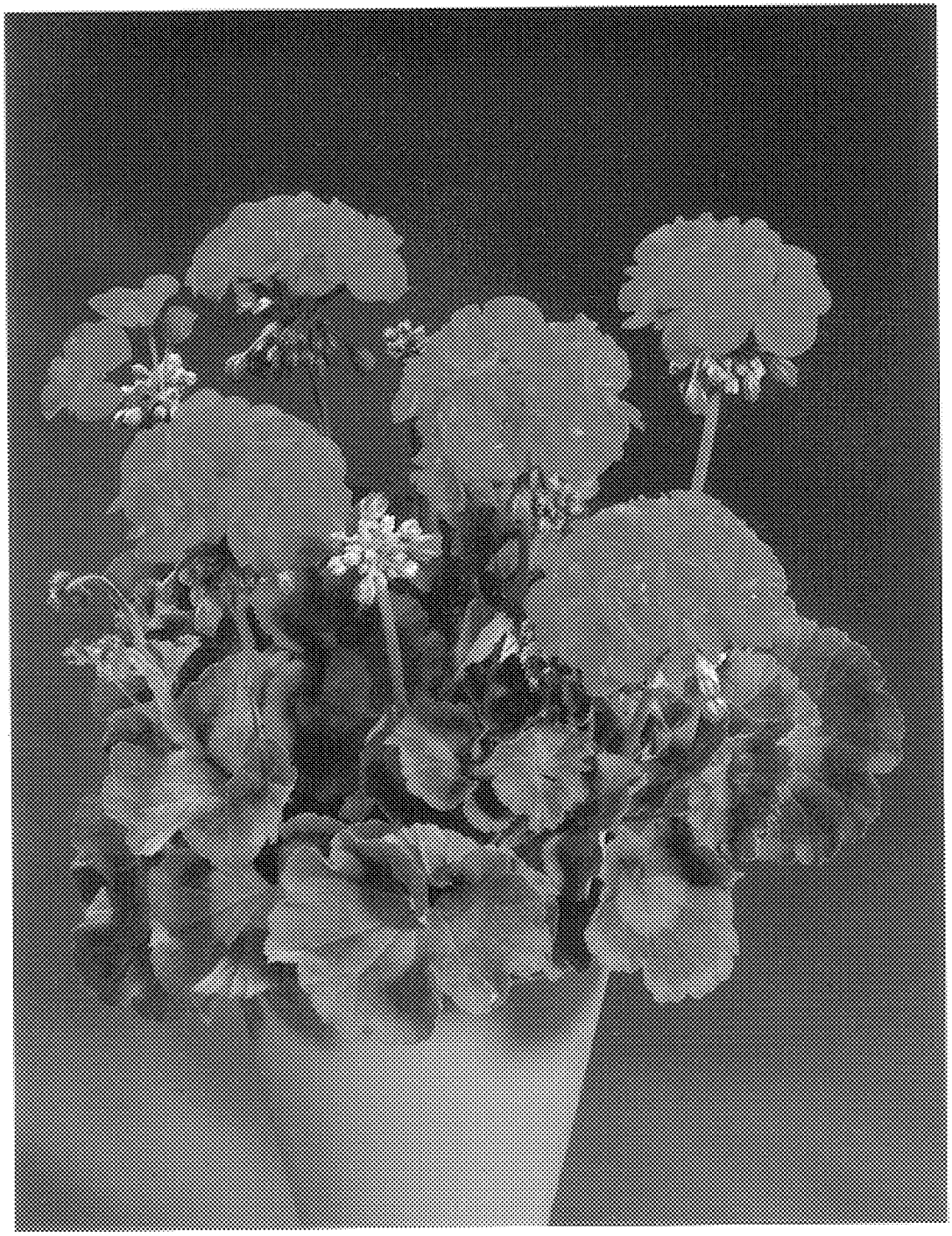

* * * * *